United States Patent [19]

Darling

[11] Patent Number: 4,537,781

[45] Date of Patent: Aug. 27, 1985

[54] PHARMACEUTICALLY USEFUL MALONAMIDES

[75] Inventor: Charles M. Darling, Auburn, Ala.

[73] Assignee: Research Corporation, New York, N.Y.

[21] Appl. No.: 533,261

[22] Filed: Sep. 16, 1983

[51] Int. Cl.³ .......................................... C07C 103/147
[52] U.S. Cl. ..................................... 514/616; 564/155
[58] Field of Search .......................... 564/155; 424/324

[56] References Cited

U.S. PATENT DOCUMENTS 4,246,279  1/1981  Bonse et al. .................... 564/155 X Primary Examiner—Paul F. Shaver
Attorney, Agent, or Firm—Scully, Scott, Murphy & Presser

[57] ABSTRACT

Compounds of the formula

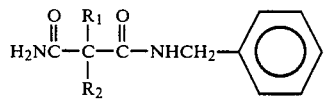

wherein $R_1$ and $R_2$ are the same or different and are hydrogen or alkyl with the proviso that $R_1$ are $R_2$ are not both hydrogen, $R_1$ and $R_2$ are preferably hydrogen or a lower alkyl of 1 to 8 carbon atoms, a pharmaceutical composition comprising an anti-epileptic effective amount of the above described compound, and a method of treating epilepsy comprising administering to a mammal an anti-epileptic amount of the above-described pharmaceutical composition.

27 Claims, No Drawings

PHARMACEUTICALLY USEFUL MALONAMIDES

FIELD OF THE INVENTION

This invention relates to new malonamide compounds and their pharmaceutical uses. More particularly, this invention relates to malonamides which exhibit anticonvulsant properties, pharmaceutical compositions comprising an effective amount of the compound of the invention for the treatment of epilepsy; and a method of treating epilepsy utilizing malonamide compositions of the present invention.

BACKGROUND OF THE INVENTION

Epilepsy refers to any of various disorders marked by disturbed electrical rhythms of the central nervous system and is typically manifested by convulsive attacks or seizures. The prevalence of epilepsy is between 3 and 6 per 1,000 of the population.

In the great majority of cases, the cause of the disease is unknown and the disease is referred to as "primary" or "idiopathic" epilepsy. When the cause is known the disease is referred to as "secondary" or "symptomatic" epilepsy. The treatment of the disease is approached essentially in the same manner for both primary and secondary epilepsy.

The therapeutic goal for treating epilepsy is to prevent seizures. If managed well with known antiepileptic drugs, approximately 75% of treated patients may have their seizures controlled or reduced in frequency. This means that there are no known drugs available to adequately treat 25% of the patients who have epilepsy. The need, therefore, exists for new antiepileptic agents.

Of the known antiepileptic drugs the major clinically useful drugs are phenytoin, phenobarbital, ethosuximide, and valproate. As stated above, these drugs are only effective on approximately 75% of epileptic patients additionally these drugs exhibit adverse side effects due to varying degrees of toxicity which exist for the drugs.

The present invention discloses that certain malonamides exhibit anticonvulsant activity. Anticonvulsant activity of these malonamides have been evidenced in tests on mice and rats. Comparative studies of anticonvulsant activity as well as toxicity, absorption characteristics and safety of malonamides as compared to four known prototype antiepileptic drugs, i.e., phenytoin, ethosuximide, phenobarbital, and valproate were performed using mice and rats as subjects. The results suggest that the malonamides have good antiepileptic potential in humans.

SUMMARY OF THE INVENTION

It is therefore an object of the present invention to provide new compounds which exhibit anticonvulsant activity and have acceptable levels of toxicity, absorption, and safety and which compounds may have potential as future antiepileptic drugs to expand therapeutic treatment, especially of patients beyond the present approximately 75% threshold, in a more complete and safe manner.

It is a further object of the invention to provide a pharmaceutical composition which utilizes an anti-epileptic effective amount of a new compound showing anticonvulsant activity. It is a still further object of the invention to provide a method for treating epilepsy by administering to a mammal an anti-epileptic effective amount of a pharmaceutical composition containing a new compound with anticonvulsant activity.

To achieve the objects in accordance with the purpose of the invention, as embodied and broadly described herein, the invention comprises compounds of the formula:

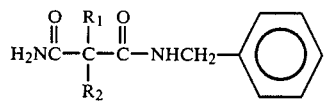

wherein $R_1$ and $R_2$ are the same or different and are hydrogen or alkyl with the proviso that $R_1$ and $R_2$ are not both hydrogen.

In a preferred embodiment of the invention, $R_1$ and $R_2$ are hydrogen or a lower alkyl of 2 to 8 carbon atoms or $R_1$ and $R_2$ are the same and are lower alkyl of 1 to 4 carbon atoms each. In a more preferred embodiment, $R_1$ and $R_2$ are the same and are methyl.

As embodied and broadly described herein, the invention also comprises a pharmaceutical composition comprising an anti-epileptic effective amount of a compound of the general formula:

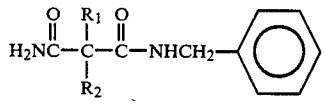

wherein $R_1$ and $R_2$ are the same or different and are hydrogen or alkyl with the proviso that $R_1$ and $R_2$ are not both hydrogen.

In a preferred embodiment of the invention $R_1$ and $R_2$ are hydrogen or a lower alkyl of 2 to 8 carbon atoms. In a further more preferred embodiment of the invention $R_1$ and $R_2$ are the same and are lower alkyl of 1 to 4 carbon atoms each. In a most preferred embodiment of the invention $R_1$ and $R_2$ are the same and are methyl.

Preferred embodiments of the pharmaceutical composition of the invention further comprise a pharmaceutical carrier, diluent, solvent, or excipient.

As embodied and broadly described herein, the invention also comprises a method of treating epilepsy comprising administering to a mammal an anti-epileptic effective amount of a pharmaceutical composition of the general formula:

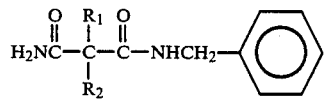

wherein $R_1$ and $R_2$ are the same or different and are hydrogen or alkyl with the proviso that $R_1$ and $R_2$ are not both hydrogen.

In a preferred embodiment of the invention, $R_1$ and $R_2$ are hydrogen or a lower alkyl of 2 to 8 carbon atoms. In a further preferred embodiment of the invention $R_1$ and $R_2$ are the same and are lower alkyl of 1 to 4 carbon atoms each. In a most preferred embodiment of the invention $R_1$ and $R_2$ are the same and are methyl.

It is to be understood that both the foregoing general and following detailed descriptions are exemplary and explanatory only and are not intended to be restrictive of the invention as claimed.

DETAILED DESCRIPTION OF THE PREFERRED EMBODIMENTS

Reference will now be made in detail to the present preferred embodiments of the invention. Examples of preferred embodiments of the invention are included at the end of this description.

In accordance with the invention the malonamides may be prepared from appropriate 2-substituted N-benzylcyanoacetamides. The acetamide starting materials may be synthesized by a modification of the method reported by Darling et al. in *J.Pharm. Sci.*, 68, 108–110(1979). The reaction scheme for the preparation of the starting nitriles is as follows:

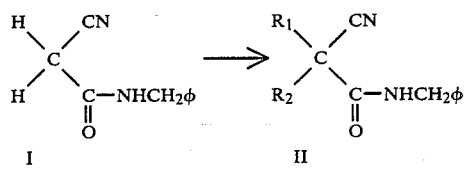

wherein $R_1$ and $R_2$ are the same or different and are hydrogen or alkyl with the proviso that $R_1$ and $R_2$ are not both hydrogen. Preferably, $R_1$ and $R_2$ are hydrogen or a lower alkyl of 2 to 8 carbon atoms or $R_1$ and $R_2$ are the same and are lower alkyl of 1 to 4 carbon atoms each. More preferably $R_1$ and $R_2$ are the same and are methyl.

The unsubstituted N-benzylcyanoacetamide (compound I) may be prepared from commonly available chemicals by the following procedure reported by O. C. Dermer and J. King, *J.Org. Chem.*, 8, 168(1943) the entire disclosure of which is incorporated herein by reference.

An article by Patel et al. in *Journal Sci. Industr. Res.*, 20B, 457, 458 (1961) reports the formation of malonmonoarylamides by partial hydrolysis of nitriles, eg. partial hydrolysis of cyanacetarylamides using polyphosphoric acid and sulfuric acid and provide further explanation of this reaction. The amides are prepared according to the following reaction:

where R is phenyl, tolyl, benzyl, xylyl and naphthyl groups.

The substituted compound (II) is prepared by alkyl addition to compound I as illustrated by the examples, supra.

The malonamides according to the invention are then prepared from the 2-substituted N-benzylcyanoacetamides (II) to produce compounds of the formula:

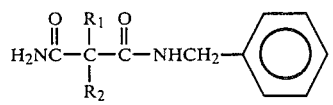

These compounds are prepared from the starting material, compound II, by partial hydrolysis of nitriles according to the known textbook method published in Royals, "Advanced Organic Chemistry", (Hall, Inc. Engelwood Cliffs, N.J. 1954, Page 595) the entire disclosure of which is incorporated herein by reference. The reaction scheme is depicted as follows:

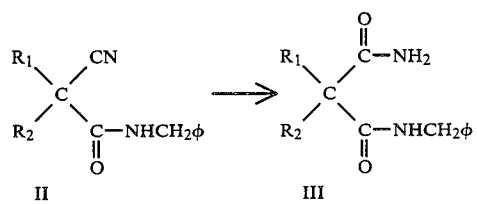

The invention will now be illustrated by examples. The examples are not intended to be limiting of the scope of the present invention. In conjunction with the general and detail descriptions above, the examples provide further understanding of the present invention.

EXAMPLE 1

To prepare the unsubstituted N-benzylcyanoacetamide (compound I) a mixture of ethyl cyanoacetate (113.1 g, 1.0 mole, obtained from Aldrich Chemical Company), benzyl amine (147 g, 1.37 mole, obtained from Eastman Chemical Products, Inc.), and ammonium chloride (16.1 g, 0.3 mole, obtained from Aldrich Chemical Company) was stirred at reflux temperature for about 6 hours. The mixture was then poured, slowly with stirring, into a mixture of ice and water (600 mls). The crude product was filtered, washed with cold water, and purified by recrystallization from 190 proof ethanol. The yield was about 75%, m.p. 121.5°–124.5°.

The substituted compound (compound II) wherein $R_1=CH_3$; and $R_2=CH_3$, may be prepared by the following procedure. To a solution of potassium hydroxide (14.0 g of 85% purity, 0.21 mole, available from Aldrich Chemical Company) in dry formamide (20 ml, available from Aldrich Chemical Company) add a solution of N-benzylcyanoacetamide (compound I) (17.4 g, 0.10 mole) in dry dimethylsulfoxide (50 ml, available from Aldrich Chemical Company) and stir at room temperature for about ½ hour. To this mixture, add, with cooling if necessary, methyl iodide (31.1 g, 0.22 mole, available from Aldrich Chemical Company) dropwise with stirring and stir at ambient temperature for about 19 hours. The mixture is then slowly added with stirring to a mixture of ice and water (200 ml). The crude product can be filtered, washed with cold water and purified by recrystallization from an appropriate solvent mixture such as petroleum ether (b.p. 30°–60°). M.P. 64°–66° C. (uncorrected).

Analyzed for $C_{12}H_{14}N_2O$: Calc.: C, 71.26%; H, 6.98%; N, 13.85%. Found: C, 71.28%; H, 6.98%; N, 13.78%.

EXAMPLES 2–11

In a manner similar to that of the above examples, the following mono- and disubstituted compounds II may be prepared. All melting points are uncorrected.

EXAMPLE 2

2-(1-Hexyl)-N-benzylcyanoacetamide (Compound II where $R_1=H; R_2=1$-hexyl), m.p. 53.5°–55.5°. Analyzed for $C_{16}H_{22}N_2O$: Calc.: C, 74.38%; H, 8.58%; N, 10.84%. Found: C, 74.18%; H, 8.52%; N, 11.04%.

EXAMPLE 3

2-Ethyl-N-benzylcyanoacetamide (Compound II where $R_1=H; R_2=$ethyl), m.p. 87°–89°. Analyzed for $C_{12}H_{14}N_2O$: Calc.: C, 71.26%; H, 6.98%; N, 13.85%. Found: C, 71.35%; H, 7.01%; N, 13.84%.

EXAMPLE 4

2-(1-Propyl)-N-benzylcyanoacetamide (Compound II where $R_1=H; R_2=$1-propyl, m.p. 83°–86°. Analyzed for $C_{13}H_{16}N_2O$: Calc.: C, 72.19%; H, 7.46%; N, 12.95%. Found: C, 72.20%; H, 7.51%; N, 12.82%.

EXAMPLE 5

2-(1-Butyl)-N-benzylcyanoacetamide (Compound II where $R_1=H; R_2=$1-butyl), m.p. 70°–72°. Analyzed for $C_{14}H_{18}N_2O$: Calc.: C, 73.01%; H, 7.88%; N, 12.16%. Found: C, 73.05%; H, 7.90%; N, 12.16%.

EXAMPLE 6

2-(1-Pentyl)-N-benzylcyanoacetamide (Compound II where $R_1=H; R_2=$1-pentyl), m.p. 59°–61°. Analyzed for $C_{15}H_{20}N_2O$: Calc.: C, 73.75%; H, 8.24%; N, 11.45%. Found: C, 73.74%; H, 8.25%; N, 11.46%.

EXAMPLE 7

2-(1-Heptyl)-N-benzylcyanoacetamide (Compound II where $R_1=H; R_2=$1-heptyl), m.p. 59°–61.5°. Analyzed for $C_{17}H_{24}N_2O$: Calc.: C, 74.96%; H, 8.88%; N, 10.28%. Found: C, 74.97%; H, 8.91%; N, 10.27%.

EXAMPLE 8

2-(1-Octyl)-N-benzylcyanoacetamide (Compound II where $R_1=H; R_2=$1-octyl), m.p. 71°–73°. Analyzed for $C_{18}H_{26}N_2O$: Calc.: C, 75.48%; H, 9.15%; N, 9.78%. Found: C, 75.49%; H, 9.15%; N, 9.77%.

EXAMPLE 9

2,2-Diethyl-N-benzylcyanoacetamide (Compound II where $R_1=R_2=$ethyl), m.p. 97°–99°. Analyzed For $C_{14}H_{18}N_2O$: Calc.: C, 73.01%; H, 7.88%; N, 12.16%. Found: C, 73.06%; H, 7.92%; N, 12.15%.

EXAMPLE 10

2,2-di(1-Propyl)-N-benzylcyanoacetamide (Compound II where $R_1=R_2=$1-propyl), m.p. 77°–79°. Analyzed for $C_{16}H_{22}N_2O$: Calc.: C, 74.38%; H, 8.58%; N, 10.84%. Found: C, 74.44%; H, 8.56%; N, 10.90%.

EXAMPLE 11

2,2-di-(1-Butyl)-N-benzylcyanoacetamide (Compound II where $R_1=R_2=$1-butyl), m.p. 76°–79°. Analyzed for $C_{18}H_{26}N_2O$: Calc.: C, 75.48%; H, 9.15%; N, 9.78%. Found: C, 75.61%; H, 9.21%; N, 9.73%.

EXAMPLES 12–22

The 2-substituted N-benzylmalonamides (Compound III) of the invention may be prepared by partial hydrolysis of the corresponding 2-substituted N-benzylcyanoacetamides (II).

EXAMPLE 12

2,2-Dimethyl-N-benzylmalonamide (Compound III; $R_1=R_2=CH_3$) may be prepared by the following procedure. Prepare a solution of the product of example 1, 2,2-dimethyl-N-benzylcyanoacetamide (24.0 g, 0.12 mole) in concentrated sulfuric acid (80 ml). After about two hours, pour the solution, slowly with stirring, into a mixture of ice and water (800 ml). The crude product may be filtered, washed with cold water, and purified by recrystallization from an appropriate solvent such as a mixture of isopropyl ether and absolute ethanol, m.p. 149°–152° (uncorrected). The yield of product should be about 50%. Analyzed for $C_{12}H_{16}N_2O_2$: Calc.: C, 65.43%, H, 7.32%; N, 12.72%. Found: C, 65.32%; H, 7.36%; N, 12.66%.

EXAMPLES 13–22

Similarly, the following 2-substituted N-benzylmalonamides (Compounds III) may be prepared.

EXAMPLE 13

2-(1-Hexyl)-N-benzylmalonamide (Compound III where $R_1=H; R_2=$1-hexyl) Starting material is product of example 2, m.p. 160°–162°. Analyzed for $C_{16}H_{24}N_2O_2$: Calc.: C, 69.53%; H, 8.75%; N, 10.14%. Found: C, 69.52%; H, 8.78%; N, 10.13%.

EXAMPLE 14

2-Ethyl-N-benzylmalonamide (Compound III where $R_1=H; R_2=$ethyl) Starting material is product of example 3, m.p. 158°–161°. Analyzed for $C_{12}H_{16}N_2O_2$: Calc.: C, 65.43%; H, 7.32%; N, 12.72%. Found: C, 65.46%; H, 7.32%; N, 12.70%.

EXAMPLE 15

2-(1-Propyl)-N-benzylmalonamide (Compound III where $R_1=H; R_2=$1-propyl) Starting material is product of example 4, m.p. 168°–170°. Analyzed for $C_{13}H_{18}N_2O_2$: Calc.: C, 66.64%; H, 7.74%; N, 11.96%. Found: C, 66.63%, H, 7.75%; N, 11.96%.

EXAMPLE 16

2-(1-Butyl)-N-benzylmalonamide (Compound III) where $R_1=H; R_2=$1-butyl) Starting material is product of example 5, m.p. 158.5°–161.5°. Analyzed for $C_{14}H_{20}N_2O_2$: Calc.: C, 67.71%; H, 8.12%; N, 11.28%. Found: C, 67.86%; H, 8.11%; N, 11.21%.

EXAMPLE 17

2-(1-Pentyl)-N-benzylmalonamide (Compound III where $R_1=H; R_2=$1-pentyl) starting material is product of example 6, m.p. 158°–161°. Analyzed for $C_{15}N_{22}N_2O_2$: Calc.: C, 68.67%; H, 8.45%; N, 10.68%. Found: C, 68.69%; H, 8.48%; N, 10.67%.

EXAMPLE 18

2-(1-Heptyl)-N-benzylmalonamide (Compound III where $R_1=H; R_2=$1-heptyl) Starting material is product of example 7, m.p. 163°–166°. Analyzed for $C_{17}H_{26}N_2O_2$: Calc.: C, 70.31%; H, 9.02%; N, 9.65%. Found: C, 70.37%; H, 9.05%; N, 9.61%.

EXAMPLE 19

2-(1-Octyl)-N-benzylmalonamide (Compound III where $R_1=H; R_2=$1-octyl) Starting material is product of example 8, m.p. 157°–159°. Analyzed for $C_{18}H_{28}N_2O_2$: Calc.: C, 71.02%; H, 9.27%; N, 9.20%. Found: C, 71.04%; H, 9.26%; N, 9.20%.

EXAMPLE 20

2,2-Diethyl-N-benzylmalonamide (Compound III where $R_1=R_2=$ethyl) Starting material is product of example 9, m.p. 142°–145°. Analyzed for $C_{14}H_{20}N_2O_2$: Calc.: C, 67.72%; H, 8.12%; N, 11.28%. Found: C, 67.78%; H, 8.14%; N, 11.28%.

EXAMPLE 21

2,2-di(1-Propyl)-N-benzylmalonamide (Compound III where $R_1=R_2=$1-propyl) Starting material is product of example 10, m.p. 105°-107°. Analyzed for $C_{16}H_{24}N_2O_2$: Calc.: C, 69.53%; H, 8.75%; N, 10.14%. Found: C, 69.57%; H, 8.76%; N, 10.10%.

EXAMPLE 22

2,2-di(1-Butyl)-N-benzylmalonamide (Compound III where $R_1=R_2=$1-butyl) Starting material is product of example 11, m.p. 87.5°-92°. Analyzed for $C_{18}H_{28}N_2O_2$: Calc.: C, 71.02%; H, 9.27%; N, 9.20%. Found: C, 70.86%; H, 9.42%; N, 9.30%.

Example 12, 2,2-dimethyl-N-benzylmalonamide, a compound according to the invention, was compared to four major clinically useful antiepileptic drugs by the epilepsy branch of the National Institute of Neurology and Communicative Disorders and Stroke and the results are reported in a document entitled "The Profile of Anticonvulsant Activity and Acute Toxicity of 56098 and Some Prototype Antiepileptic Drugs in Mice and Rats" which report is dated 7/2/82 and numbered as 38. The entire disclosure of which is incorporated herein by reference. 56098 was the designation for 2,2-dimethyl-N-benzylmalonamide which is present example 12. A critical comparative study was carried out for the anticonvulsant activity, toxicity, absorption characteristics, and safety of 2,2-dimethyl-N-benzylmalonamide, example 12, in comparison to phenytoin, phenobarbital, ethosuximide and valproate the results of which are summarized in the following Table I.

TABLE I

| Compound | Anticonvulsant Activity | | Toxicity |
| --- | --- | --- | --- |
| | MES[1] | Sc Met[2] | |
| 2,2-dimethyl-N—benzylmalonamide* (Example 12) | Significant | Significant | medium toxicity |
| phenobarbital° | Significant | Significant | most toxicity |
| Valproate° | Significant | Significant | least toxicity |
| Phenytoin° | Significant | none | most toxicity |
| Ethosuximide° | None | Significant | least toxicity |

*Administered in requisite volume of 30% polyethylene glycol 400
°Administered in 0.9% sodium chloride solution
[1]MES is maximal electroshock seizure
[2]Sc Met is subcutaneous metrazol seizure As indicated in Table I, example 12 of the invention was found to possess good anticonvulsant activity and low toxicity levels. Further, the compound had acceptable safety and absorption characteristics.

The results of testing in mice and rats indicates that the subject compound of the invention has a potential of being useful in most of the epilepsies including the now untreatable and difficult to control cases, as well as being less toxic and safer than those known drugs against which it was tested.

The compound was found to be effective both orally and intraperitoneally in mice and rats and the dosage was comparable to that of the prototype drugs in mice and rats.

In preparing pharmaceutical compositions utilizing the compound of the invention additional ingredients can be added such as a pharmaceutical carrier, diluent or solvent. Additionally, the pharmaceutical composition may include an excipient.

The scope of the present invention is not limited by the description, examples and suggested uses herein, and modifications can be made without departing from the spirit of the invention. For example, compounds of the present invention may be combined with other therapeutic agents to form a pharmaceutical composition that has a broader range of application than would either of the therapeutic agents have on its own. Thus, it is intended that the present invention cover the modifications and variations of this invention provided they come within the scope of the appended claims and their equivalents.

What is claimed is:

1. A compound of the formula

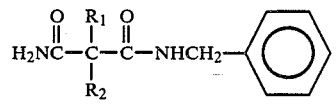

wherein $R_1$ and $R_2$ are the same or different and are hydrogen or alkyl with the proviso that $R_1$ and $R_2$ are not both hydrogen.

2. A compound according to claim 1 wherein $R_1$ and $R_2$ are hydrogen or a lower alkyl of 2 to 8 carbon atoms.

3. A compound according to claim 1 wherein $R_1$ and $R_2$ are the same and are lower alkyl of 1 to 4 carbon atoms each.

4. A compound according to claim 1 wherein $R_1$ and $R_2$ are the same and are methyl.

5. A compound according to claim 1 wherein $R_1$ and $R_2$ are the same and are ethyl.

6. A compound according to claim 1 wherein $R_1$ and $R_2$ are the same and are n-propyl.

7. A compound according to claim 1 wherein $R_1$ and $R_2$ are the same and are n-butyl.

8. A compound according to claim 1 wherein $R_1$ is hydrogen and $R_2$ is ethyl.

9. A compound according to claim 1 wherein $R_1$ is hydrogen and $R_2$ is 1-propyl.

10. A compound according to claim 1 wherein $R_1$ is hydrogen and $R_2$ is 1-butyl.

11. A compound according to claim 1 wherein $R_1$ is hydrogen and $R_2$ is 1-pentyl.

12. A compound according to claim 1 wherein $R_1$ is hydrogen and $R_2$ is 1-hexyl.

13. A compound according to claim 1 wherein $R_1$ is hydrogen and $R_2$ is 1-heptyl.

14. A compound according to claim 1 wherein $R_1$ is hydrogen and $R_2$ is 1-octyl.

15. A pharmaceutical composition comprising an anti-epileptic effective amount of a compound of the general formula:

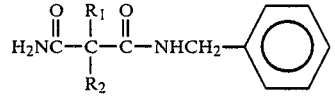

wherein $R_1$ and $R_2$ are the same or different and are hydrogen or alkyl with the proviso that $R_1$ and $R_2$ are not both hydrogen in association with a pharmaceutical carrier.

16. A pharmaceutical composition according to claim 15 wherein $R_1$ and $R_2$ are hydrogen or a lower alkyl of 2 to 8 carbon atoms.

17. A pharmaceutical composition according to claim 15 wherein $R_1$ and $R_2$ are the same and are lower alkyl of 1 to 4 carbon atoms each.

18. A pharmaceutical composition according to claim 15 wherein $R_1$ and $R_2$ are the same and are methyl.

19. A pharmaceutical composition according to claim 15 additionally comprising an excipient.

20. A method of treating epilepsy comprising administering to a mammal an anti-epileptic effective amount of a compound of the general formula:

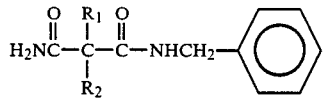

wherein $R_1$ and $R_2$ are the same or different and are hydrogen or alkyl with the proviso that $R_1$ and $R_2$ both are not hydrogen.

21. A method according to claim 20 wherein $R_1$ and $R_2$ are hydrogen or a lower alkyl of 2 to 8 carbon atoms.

22. A method according to claim 20 wherein $R_1$ and $R_2$ are the same and are lower alkyl of 1 to 4 carbon atoms each.

23. A method according to claim 20 wherein $R_1$ and $R_2$ are the same and are methyl.

24. A method according to claim 20 additionally comprising a pharmaceutical carrier, diluent or solvent.

25. A method according to claim 24 additionally comprising an excipient.

26. A method according to claim 24 wherein the pharmaceutical composition is administered parenterally.

27. A method according to claim 24 wherein the pharmaceutical composition is administered orally.

* * * * *